(12) United States Patent
Riihimäki

(10) Patent No.: US 7,850,986 B2
(45) Date of Patent: Dec. 14, 2010

(54) DELIVERY SYSTEM

(75) Inventor: Teppo Riihimäki, Turku (FI)

(73) Assignee: Schering Oy, Turku (FI)

( * ) Notice: Subject to any disclaimer, the term of this patent is extended or adjusted under 35 U.S.C. 154(b) by 781 days.

(21) Appl. No.: 11/631,873

(22) PCT Filed: Jul. 5, 2005

(86) PCT No.: PCT/FI2005/000314

§ 371 (c)(1),
(2), (4) Date: Jan. 8, 2007

(87) PCT Pub. No.: WO2006/005794

PCT Pub. Date: Jan. 19, 2006

(65) Prior Publication Data

US 2008/0031922 A1    Feb. 7, 2008

(30) Foreign Application Priority Data

Jul. 13, 2004   (EP) .................. 04396049

(51) Int. Cl.
*A61F 6/06*     (2006.01)
*A61F 6/14*     (2006.01)

(52) U.S. Cl. ..................... 424/430; 424/432

(58) Field of Classification Search .................. None
See application file for complete search history.

(56) References Cited

U.S. PATENT DOCUMENTS

| | | | |
|---|---|---|---|
| 4,985,253 A | 1/1991 | Fujioka et al. | 424/488 |
| 5,492,947 A * | 2/1996 | Wood et al. | 524/48 |
| 5,788,980 A | 8/1998 | Nabahi | 424/430 |
| 6,039,968 A * | 3/2000 | Nabahi | 424/433 |
| 6,299,894 B1 | 10/2001 | Markkula et al. | 424/422 |
| 6,416,778 B1 | 7/2002 | Ragavan et al. | 424/430 |
| 2001/0029357 A1 | 10/2001 | Bunt et al. | 604/265 |
| 2002/0161352 A1 | 10/2002 | Lin et al. | 604/515 |
| 2003/0059456 A1 | 3/2003 | Malcolm et al. | 424/430 |
| 2004/0010224 A1 | 1/2004 | Bodmeier | 604/82 |
| 2004/0265355 A1 | 12/2004 | Shalaby | 424/426 |

FOREIGN PATENT DOCUMENTS

| | | |
|---|---|---|
| EP | 0 303 306 | 2/1989 |
| EP | 1 629 844 | 3/2006 |
| RU | 2 088 166 | 8/1997 |
| WO | WO 95/27481 | 10/1995 |
| WO | WO 99/61062 | 12/1999 |
| WO | WO 01/85133 | 11/2001 |
| WO | WO 02/32433 | 4/2002 |
| WO | WO 03/017971 | 3/2003 |
| WO | WO 2005/004837 | 1/2005 |
| WO | WO 2005/089723 | 9/2005 |

OTHER PUBLICATIONS

Quaglia et al., 86 *J. Controlled Release* 267-278 (2003).
Ikeda et al., "Controlled Release of a Water-soluble Drug, Captopril, by a Combination of Hydrophilic and Hydrophobic Cyclodextrin Derivatives," 66 *J. Controlled Release* 271 (2000).

* cited by examiner

*Primary Examiner*—Robert A Wax
*Assistant Examiner*—Lyndsey Beckhardt
(74) *Attorney, Agent, or Firm*—James C. Lydon

(57) ABSTRACT

The present invention relates to a delivery system comprising a core and a membrane encasing said core, wherein said core and membrane consist essentially of an elastomer composition and said core comprises at least one therapeutically active agent. The delivery system is characterized in that the membrane comprises at least one regulating agent. The invention also relates to a method for controlling the release of at least one therapeutically active agent from a delivery system.

7 Claims, 3 Drawing Sheets

DELIVERY SYSTEM

FIELD OF THE INVENTION

The present invention relates to a delivery system comprising a core and a membrane encasing said core, wherein said core and membrane consist essentially of an elastomer composition and said core comprises at least one therapeutically active agent. The present invention also relates to a method for controlling the release of at least one therapeutically active agent from a delivery system comprising a core and a membrane encasing said core, wherein said core and membrane consist essentially of an elastomer composition and said core comprises said at least one therapeutically active agent.

BACKGROUND OF THE INVENTION

The publications and the material used herein to illuminate the background of the invention and, in particular, cases to provide additional details respecting the practice, are incorporated by reference.

The use of drug delivery systems for the delivery of a therapeutically active agent, which systems provide for steady release of a therapeutically active agent to a patient's body at a controlled rate over a prolonged period of time in order to achieve a desired physiological or pharmacological effect, have proved beneficial in many therapeutic areas. A principal advantage of employing sustained-release compositions is that many therapeutically active agents would otherwise be rapidly metabolised or cleared from the patient's body, thus necessitating frequent administration of the therapeutically active agent to maintain a therapeutically effective concentration.

A problem often faced in controlling the release of the therapeutically active agent by using a slow releasing preparation is initial burst, i.e. the release of a relatively large amount of the therapeutically active agent right after the preparation has been administered or inserted to the patient. If such an initial burst occurs, the concentration of the therapeutically active agent in the blood may exceed the permissible upper limit, which may be dangerous to the patient. Initial burst can be prevented to a certain extent by selecting the form of the therapeutically active agent and the releasing material, but a basic solution for preventing initial burst has been the subject of extensive studies. On the other hand, the concentration of a therapeutically active agent in a preparation should be as high as possible in order to achieve slow release of the therapeutically active agent over a long period of time and to be able to maintain a moderate size of the preparation.

The initial burst may be decreased or avoided by modifying the physical state of the active agent. The therapeutically active agent can be incorporated into a controlled release agent, such as polymer microspheres, which steadily or intermittently release the therapeutically active agent. Examples of suitable controlled release components include microstructures, such as microparticles, nanoparticles, cyclodextrins, microcapsules, micelles and liposomes. The controlled release component may also include macrostructures. Suitable controlled release components also include salts of the therapeutically active agent and complexes or conjugates in which the therapeutically active agent is operatively associated with a carrier molecule.

For the liquid delivery compositions, which typically include a biodegradable and/or bioerodable polymer or copolymer dissolved in a non-toxic organic solvent, the additional time required to release the therapeutically active agent from the controlled release component will enable the formulation to solidify into a solid implant without the initial loss of a substantial amount of the therapeutically active agent. Once formed into a solid matrix, the permeation of the therapeutically active agent is based on the rates the therapeutically active agent is released from the controlled release component and from the implant matrix. The second mode is governed by the rate of biodegradation and/or bioerosion of the implant material.

On the other hand, in making the polymer microspheres the controlled release components, such as cyclodextrin, also serve as a buffer and reduce denaturing of a sensitive therapeutically active agent, e.g. when the microspheres are compressed into pellets. The buffers usually dissolve more quickly than the polymer and hereby facilitate the release of the therapeutically active agent by creating tunnels in the microspheres Inclusion of the controlled release components can therefore also lead to an initial burst of drug release after implantation.

A variety of methods for achieving low initial burst of formulations of therapeutically active agents have been described in the literature. Such methods have mainly been focused in injection delivery systems, such as microparticles, liquid polymer compositions and gel compositions.

International Patent Application WO 95/27481 A1 is related to liquid polymer compositions that are useful for the delivery of therapeutically active agents in vivo and permit the initial burst to be controlled more effectively than previously possible. When a liquid delivery system including a biodegradable polymer and a therapeutically active agent dissolved in a water-soluble solvent comes into contact with an aqueous medium, such as a body fluid, the solvent dissipates or diffuses into the aqueous medium. As the polymer precipitates or coagulates to form a solid matrix, the active agent is trapped or encapsulated throughout the polymeric matrix. The release of the active agent then follows the general rules for the dissolution or diffusion of a therapeutically active agent from within a polymeric matrix. The formation of the solid matrix from the liquid delivery system is, however, not instantaneous but typically occurs over a period of several hours. During this initial period, the rate of diffusion of the active agent may be much more rapid than the rate of release that occurs from the subsequently formed solid matrix. The initial burst can be decreased by incorporating the active agent into a controlled release component and combining the controlled release component with the liquid polymer systems described for example in U.S. Pat. Nos. 4,938,763, 5,278,201 and 5,278,202.

International Patent Application WO 01/08717 A1 is related to implantable devices, where the therapeutically active agent is incorporated into a controlled release agent, such as polymer microspheres, which steadily or intermittently release the therapeutically active agent. Various polymers can be used for encapsulating therapeutically active agents in microspheres. Preferably, the polymers are biocompatible and degradable when placed within human tissue. In the preparation of the microspheres, buffers, such as sucrose and cyclodextrin, can be added. Inclusion of buffers is, however shown to lead to an initial burst of the active agent during, e.g., the first 24 hours after implantation.

International Patent Application WO 96/01626 A1 is related to a transdermal system comprising a reservoir with the therapeutically active agent in ionized form, a pH adjusting agent and a cyclic polysaccharide for improving the solubility of the therapeutic agent in the buffer solution. The polysaccharide may be selected from a group consisting of cyclodextrin or a derivative thereof and a cyclodextrin polymer. The reservoir wall comprises a polymer, which is substantially impermeable to the ionized form or the inclusion complex of the therapeutically active agent, but is permeable to water and to the unionized form of the therapeutically active agent. The therapeutically active agent is able to penetrate through the reservoir wall only when the system is applied to the skin and water penetrates through the reservoir wall into the core. During these initial stages the release rate of the therapeutically active agent slowly increases until the concentration of the therapeutically active agent in the reservoir wall reaches steady-state levels. The delay before steady levels are achieved in plasma can be avoided by loading the reservoir wall of a single core reservoir system with the therapeutically active agent to give a priming dose of the therapeutically active agent. The loading of the reservoir wall can cause an initial burst. The magnitude of the burst or delay in the release of the therapeutically active agent can be modified by varying the amount of the therapeutically active agent that is loaded.

A publication of J Biomater Sci Polym Ed. 1994;5(4):339-51 describes controlled release systems prepared from biodegradable microparticles of poly(lactic acid-co-glycolic acid) containing beta-estradiol in the presence or absence of silicone. The release behaviour of beta-estradiol from free microparticles as well as from microparticles embedded within a silicone matrix is compared with the release behaviour shown by non-encapsulated beta-estradiol within a silicone matrix. It was found that incorporating biodegradable microparticles within a silicone matrix lessens the initial burst of release often seen with these types of formulations and provides a controlled release of therapeutically active agent.

The above applications concentrate on injectable formulations, wherein the controlled release or regulating material and the therapeutically active agent are located in the same phase of the delivery system.

Document US 2002/0161352 presents a vaginal ring preparation comprising a tubular base of an inert rubber, a first layer on top of it comprising a drug, a surfactant and a dispersing agent as well as a second layer of silicone rubber encapsulating said first layer on the tubular base. The dispersing agent may be for example R-type or B-type cyclodextrin. Thus this document does not disclose a core-membrane-structure wherein the therapeutically active agent is comprised in the core.

The initial burst effect, i.e. the amount of therapeutically active agent typically released in the first 24-48 hours, is non-efficient by resulting in the loss or release of a relatively large amount of the therapeutically active agent. If the therapeutically active agent is not well tolerated, this initial burst is likely to lead to side effects and may cause damage to the adjacent tissues. In any of the above cases, these effects may prohibit the use of that certain formulation, if the burst effect cannot be minimized.

The development of delivery systems with reduced or eliminated initial burst effect would represent a significant advancement. The efficiency of such systems would be improved, since a greater percentage of the active agent would remain in the device for sustained release and not be lost during the initial burst. The possibility of side effects would be reduced. There is, therefore, a continuing need for controlled release systems that will facilitate the sustained release of a therapeutically active agent in a patient's body without creating an initial burst of therapeutically active agent.

OBJECT AND SUMMARY OF THE INVENTION

An object of the present invention is to provide a system and method for controlling the initial burst of therapeutically active agent from a delivery system that consists of at least one elastomer.

One object of the present invention is further to provide a system intended for the administration of a therapeutically active agent at a substantially constant release rate for a prolonged period of time, said system comprising a core and a membrane encasing said core, wherein said core and membrane consist essentially of an elastomer composition.

One object is particularly to provide a delivery system in which the release rate of the therapeutically active agent and the initial burst can easily be adjusted.

Another object of this invention is to provide a delivery system in the form of an implant, intravaginal device, intracervical or intrauterine device or transdermal patch intended for the administration of said therapeutically active agent.

Still another object is to provide a safe and flexible releasing system, which has a small cross section and which is easy to insert and convenient to wear.

Thus, the present invention concerns a delivery system and a method as described below in the independent claims.

A typical delivery system according to the present invention comprises a core and a membrane encasing said core, wherein said core and membrane consist essentially of an elastomer composition and said core comprises at least one therapeutically active agent. The membrane comprises at least one regulating agent.

A typical method according to the present invention is a method for controlling the release rate of at least one therapeutically active agent from a delivery system comprising a core and a membrane encasing said core, wherein said core and membrane consist essentially of an elastomer composition and said core comprises at least one therapeutically active agent. The regulation is performed by at least one regulating agent comprised in the membrane of said delivery system.

DETAILED DESCRIPTION OF THE INVENTION

Figure 1:
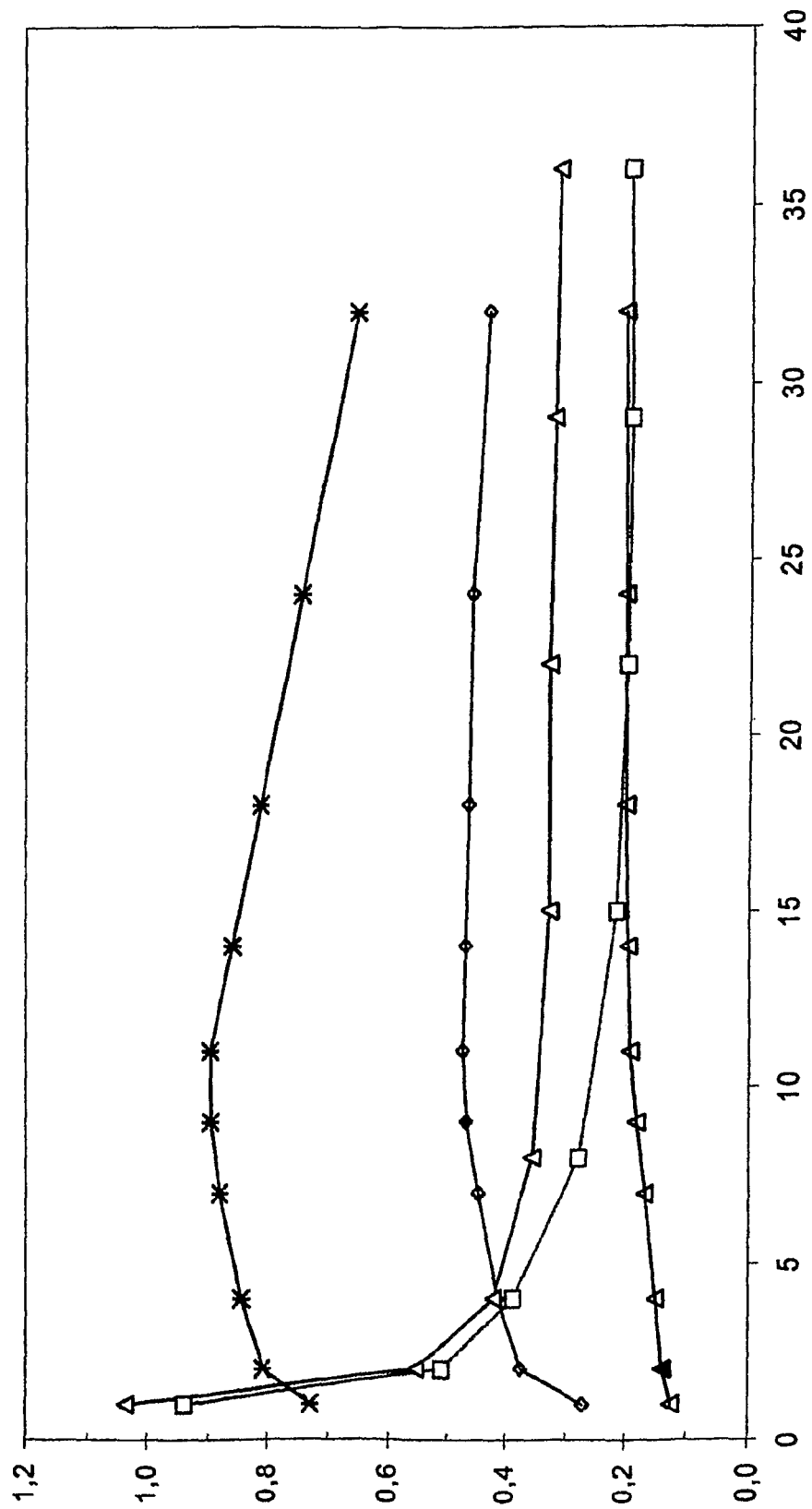
FIG. 1 illustrates the results of example 1.

The present invention concerns a delivery system and a method as described below in the independent claims. The dependent claims illustrate some embodiments of the invention.

A typical delivery system according to the present invention comprises a core and a membrane encasing said core, wherein said core and membrane consist essentially of an elastomer composition and said core comprises at least one therapeutically active agent. The membrane comprises at least one regulating agent.

The regulating agent is capable of forming chemical bonds, complexes or conjugates or binding with the therapeutically active agent molecules and immobilizing or binding them into the membrane. All of these ways of association are intended to be temporary, thus inhibiting or lowering the release at the beginning.

In this description, the term "therapeutically active agent" is often used in singular. It is to be understood that the same given details apply when several therapeutically active agents are used.

The invention is thus based on the fact that initial burst of therapeutically active agent(s) can be controlled and adjusted by adding at least one regulating agent selected from certain types of compounds in the membrane of a delivery system that is capable of forming chemical bonds, complexes or conjugates, in which the therapeutically active agent is operatively associated with a regulating agent, immobilizing or binding with the therapeutically active agent molecules first to be released, immobilizing or binding them into the membrane and thus prohibiting the burst effect. The regulating agent itself can be bound into membrane material physically or chemically.

The present invention is therefore related to delivery applications for controlling the release rate of a therapeutically active agent over a prolonged period of time and starting from the beginning of therapy to achieve a low initial burst of the therapeutically active agent or no burst at all. In such applications, a release rate over a prolonged time can be adjusted by changing the formulation materials, physical dimensions and therapeutically active agent load of the system. The burst effect, where the initial release of the therapeutically active agent can be several times higher than the later achieved zero-order release, cannot, at the time of making the present invention, be fully adjusted by changing only the formulation of the device.

In the present invention the burst preventing regulating material is located in the membrane encasing the core or container comprising the therapeutically active agent. The low initial burst is achieved by a formation of chemical bonds, complexes, conjugates or weak intermolecular bonds between the regulating agent and the molecules of the therapeutically active agent first to be released of the core material, and binding them into the membrane and thus prohibiting the burst effect. The present invention introduces a method of adjusting burst phenomena and acquiring a negative burst effect at its best. In a negative burst effect, the release rate of the therapeutically active agent is steadily accelerating from zero, reaching smoothly the normal release rate instead of being much higher at the very beginning of the release and then decreasing from there to the normal therapeutic window.

A typical method according to the present invention is a method for controlling the release rate of at least one therapeutically active agent from a delivery system comprising a core and a membrane encasing said core, wherein said core and membrane consist essentially of an elastomer composition and said core comprises said at least one therapeutically active agent. The regulation is performed by at least one regulating agent comprised in the membrane of said delivery system.

The regulating agent can be bound into the membrane elastomer physically, depending on its size difference compared to the membrane elastomer network, or chemically into the membrane elastomer chains.

The term "regulating agent" is used here to mean the burst-controlling agent, which comes into contact with the releasing therapeutically active agent. The regulating agent can be any substance, which is capable of forming chemical bonds, complexes or conjugates with the releasing therapeutically active agents, or capable of forming one or more host-guest associations via nonbonding interactions with the therapeutically active agents, e.g. via van der Waals forces, hydrogen bonding, dipole-dipole interactions or ion-paring, and can be bound into the elastomer network physically or chemically directly into the polymer chains.

According to an embodiment of the present invention, said regulating agent is selected from the group consisting of carbohydrates, cyclodextrins and modified cyclodextrins. According to another embodiment of the present invention, said regulating agent is selected from the group consisting of alpha cyclodextrins, beta cyclodextrins, gamma cyclodextrins, hydroxypropyl cyclodextrins, maltosyl β-cyclodextrin, β-cyclodextrin sulfobutyl ether and a cyclodextrin polymer.

Other applicable regulating agents include plant extrudates such as gum arabic, seaweed extracts such as agar, guar gum, starches, fermentation gums such as dextran, animal products such as gelatin, cellulose derivatives such as hydroxyalkyl celluloses, carboxymethylcelluloses, carboxylic derivatives of cellulose, glycerol esters, mono- or polyglycerides, pectins, carrageenan, polyethylene glycol, liposomes, alginates, albumin and sorbitan fatty acid esters and crown ethers.

For pharmaceutical uses, the regulating agent should have a low toxicity profile and should preferably not be toxic. Particularly useful regulating agents are therefore cyclodextrins ($\alpha$, $\beta$ or $\gamma$) and cyclodextrin derivatives.

With cyclodextrins the essential part of complex formation is the hydrophobic cavity of the molecule, which binds hydrophobic therapeutically active agents.

The control of the initial release of a therapeutically active agent can be achieved in several ways. First, the molar content of reacting agent in the membrane can be adjusted with respect to the amount of molecules of active agent released in the initial burst. Secondly, the particle size of the regulating agent in the membrane elastomer can be adjusted as well, as the particle size influences the distribution (more or less equal distribution) of the regulating agent in the membrane. Finally, the stability of the complex or conjugate between the regulating agent and the therapeutically active agent can also be one method of controlling the initial release of the therapeutically active agent. The initial burst can be adjusted by changing the regulating agent, e.g. by using hydroxypropyl modified cyclodextrin instead of cyclodextrin.

With cyclodextrins, a powder form substance can be dissolved into ethanol to mix it homogeneously into the membrane polymer. In that case ethanol must be removed after mixing, by vacuum or heat depending on the crosslinking method of the elastomer material.

According to an embodiment of the present invention, the membrane comprises one regulating agent. According to another embodiment, the membrane comprises two regulating agents. The membrane may also comprise any other number of regulating agents, such as three, four, five, six, seven, eight or more different regulating agents. The amount of different regulating agents can be the same or different.

The formulation of the present invention is intended to mean the physical structure, i.e. size, dimensions and shape of the core and membrane parts of the system as well as the therapeutically active agent, which is loaded in the core part. The system can be an implant, an intravaginal ring, an intracervical device, an intrauterine system (IUS), a transdermal device or any non specified type of device having an implant type structure. The system can also comprise individual parts without any membrane or core. Such parts are for example the ends of the implant, which can be sealed with any biocompatible material without the therapeutically active agent. The system can also consist of a pharmaceutically inactive body or any separate part of the system to improve the strength of the structure or to help the insertion or attachment of the system into any point of body.

The core and the membrane encasing said core consist essentially of a same or different elastomer composition.

The elastomer composition used in the membrane is such that it allows the pre-determined, constant release rates of the therapeutically active agent(s). The regulating agent(s) added in the membrane elastomer material allow the adjustment of the initial release rate, i.e. the release rate before the constant release is achieved. The main object of the invention is thus obtained by the choice of the regulating agent(s).

The core consists essentially of an elastomer composition, that is, the core is an elastomer matrix, wherein the therapeutically active agents are dispersed. Therefore, even if the membrane encasing the core would be damaged, the therapeutically active agents would not be released in a completely uncontrolled manner causing side effects to the patient. The elastomer composition of the core is thus chosen so that the membrane primarily regulates the release of the therapeutically active agent. The release rates in general can be controlled by the membrane alone or by the membrane together with the core. It is also possible that the release rate is mainly controlled by the core.

The core may consist of one part comprising a therapeutically active agent as such, e.g. in liquid or crystallized form or optionally in combination with other therapeutically active agents. Alternatively, the core can consist of the therapeutically active agent or agents in a mixture with pharmaceutically acceptable excipients.

According to another embodiment of the invention, the core consists of at least two parts each part comprising at least one therapeutically active agent. The elastomer compositions of said parts are chosen according to the release rates desired and can be the same or different in each part. According to the embodiment in which the core consists of two or more parts, the parts may be either positioned next to each other or in such a way that one part of a core encases at least partly another part of the core. Any combination of structure is naturally possible and within the scope of the invention. If several parts of core are used, the different parts may or may not be separated from each other by a separation membrane.

The membrane may consist of one or more layers, such as one, two three, four, five, six or seven layers. According to an embodiment of the invention, the membrane consists of at least two layers, each layer having a certain thickness. The thickness of the layers may be the same or different and the elastomer compositions used in each layer may also be the same or different. The membranes encasing each above-mentioned part of the core may also be identical or different in either the elastomer composition or the structure of the membrane (one or several layers). The combination of different layers of membrane either in thickness or in material or both gives a further possibility for controlling the release rates of the therapeutically active agents.

Depending on the application used for the delivery of a therapeutically active agent and the number of therapeutically active agents, one or more regulating agents can be used, as discussed above. The regulating agents can be in the same membrane but they can also be placed into separate parts of the membrane and/or in separate layers of the membrane.

Elastomer compositions mentioned above, namely the elastomer compositions of the core, the membrane and the possible separation membrane, can be the same or different and may stand for one single elastomer, or the elastomer composition may be made up of elastomers that are interlaced, one inside the other. The term "elastomer" is intended to mean at least partly amorphous polymer or a mixture of polymers, the deformation of which caused by the strain is reversible, i.e. the elastomer's shape recovers to a certain level after the strain.

In principle any elastomer can be used as a carrier as long as it is biocompatible. However, the release kinetics of a therapeutically active agent from an elastomeric delivery system depend on the molecular weight, solubility, diffusivity and charge of the therapeutically active agent as well as the characteristics of the elastomer, the percentage of the loading of the therapeutically active agent, the distance the therapeutically active agent must diffuse through the device body to reach its surface and the characteristics of any matrix or membrane.

Examples of commonly used polymeric materials include, but are not limited to, polysiloxanes, ethylene/vinyl acetate copolymers (EVA), and copolymers of dimethylsiloxanes and methylvinylsiloxanes. The structural integrity of the material may be enhanced by the addition of a particulate material such as silica or diatomaceous earth. The elastomers can also be mixed with other additives to adjust elastomer's hydrophilic or hydrophobic properties while taking into account that they need to be biocompatible and harmless to the patient.

According to a preferable embodiment, the core is made of a siloxane based elastomer composition comprising at least one elastomer and possibly a non-crosslinked polymer.

The elastomer composition may also be selected from the group consisting of
- an elastomer composition comprising poly(dimethylsiloxane) (PDMS),
- an elastomer composition comprising a siloxane-based elastomer comprising 3,3,3-trifluoropropyl groups attached to the Si-atoms of the siloxane units,
- an elastomer composition comprising poly(alkylene oxide) groups, said poly(alkylene oxide) groups being present as alkoxy-terminated grafts or blocks linked to the polysiloxane units by silicon-carbon bonds or as a mixture of these forms, and
- a combination of at least two thereof.

According to an embodiment of the invention, in the siloxane-based elastomer 1 to approximately 50% of the substituents attached to the Si-atoms of the siloxane units are 3,3,3-trifluoropropyl groups. The percentage of the substituents that are 3,3,3-trifluoropropyl groups can be for example 5-40%, 10-35%, 1-29% or 15-49.5%.

According to another embodiment of the invention, the poly(alkylene oxide) groups mentioned above are poly(ethylene oxide) (PEO) groups.

The methods for the preparation of these elastomers are given in the applicant's other patents and patent applications.

Different Types of Systems

The system can be any system suitable for delivery of the therapeutically active agent at a controlled rate over a prolonged period of time. Thus, the system can take a wide variety of shapes and forms for administering the therapeutically active agent at controlled rates to different areas of the body. The invention can be applied to any type of formulation as long as they consist of a membrane controlling the release of a therapeutically active agent and a core containing the therapeutically active agent. The invention includes external and internal drug delivery systems, such as transdermal patches, implants for releasing a therapeutically active agent in the body tissues, intravaginal rings, intracervical and intrauterine devices.

According to a preferred embodiment, the device is an implant for subcutaneous use, an intravaginal ring or an intrauterine system (IUS). According to the most preferred embodiments, the device is an implant for subcutaneous use or an intrauterine system.

The manufacturing of such systems is discussed below, even though it is well known in the art. The shape and size of the system may also be freely chosen by the person skilled in the art. It is also evident that the systems according to the invention may be applied to humans as well as to animals. When the delivery system is for example an intrauterine system, it may further comprise a body forming the structure of the system, which can be made of any biocompatible material. In this case, the core-membrane structure of the system is hollow so that it can be positioned over the body of the system. The body may have various forms, e.g. the form of T, S or 7.

The Therapeutically Active Agent

The variety of different therapeutically active agents can be used in conjunction with the invention. Therapeutically active agents can be mixed as such with above materials or they may be used in liquid form mixed with suitable diluents such as polyethylene glycol (PEG).

The amount of the therapeutically active agent incorporated in the delivery system varies depending on the particular therapeutically active agent, the desired therapeutic effect and the time for which the system is expected to provide therapy. Since a variety of devices with varying sizes and shapes can be formulated for administering dosages for different therapeutical areas, there is no critical upper limit on the amount of therapeutically active agent incorporated in the device. The lower limit depends on the activity of the therapeutically active agent and the expected release time. A person skilled in the art is readily able to determine the amount of the therapeutically active agent needed for each specific application of the delivery system.

Preferably, the amount of therapeutically active agent in the core varies between almost zero to 70 wt-%, when it is mixed into the elastomer, the preferred amount being between 20-60 wt-%. Other possible ranges of the amount of the therapeutically active agent are 0,5-70 wt-%, 5-65 wt-%, 10-50 wt-%, 25-70 wt-%, 50-60 wt-% and 40-50 wt-%. The core can also consist of pure therapeutically active agent, which however is not recommended due to a risk of system breakage.

Manufacture of Implants

The implants according to this invention can be manufactured in accordance with standard techniques. The therapeutically active agent is mixed with the core matrix elastomer, such as polydimethylsiloxane (PDMS), or the components forming the elastomer composition as defined above, processed to the desired shape by molding, casting, extrusion, or other appropriate methods. The membrane layer can be applied onto the core according to known methods, such as by mechanical stretching, swelling in a suitable solvent, such as cyclohexane, diglyme, isopropanol, or mixture of solvents, or dipping. Reference is made to the patents U.S. Pat. Nos. 3,832,252, 3,854,480 and 4,957,119. An especially suitable method for preparation of the implants is disclosed in the Finnish patent FI 97947. This patent discloses an extrusion technology, where prefabricated rods containing the active ingredient are coated by an outer membrane. Each such rod is, for example, followed by another rod without any active ingredient. The formed string is cut at the rods that contain no active agent. In this way, no special sealing of the ends of the implant is necessary.

Intravaginal ring and the medicated cores used in intrauterine and intracervical systems represent one application of an implant and can be manufactured by using similar techniques.

Intrauterine and Intracervical Systems

The intrauterine system can be made according to well-known technology. A preferable intrauterine system (IUS) or intracervical system in common use is a T-shaped body made of plastic material such as polyethylene. The body consists of an elongate member (stem) having at one end a transverse member comprising two wings. The elongate member and the transverse member form a substantially T-shaped piece when the device is positioned in the uterus. The device has an attached thread long enough to protrude out of the cervical canal when the device is in position in the uterus. In medicated intrauterine systems the therapeutically active agent intended to be released is in a core or a reservoir adjusted around the body. The core or reservoir preferably consists of the elastomer matrix with the therapeutically active agent dispersed therein. The matrix is encased in a membrane that is made of an elastomer.

The reservoir adjusted around the stem of the T-shaped body can be manufactured by using methods described above for the manufacture of implants. Alternatively, the matrix can first be applied onto the stem after which the matrix is encased by a membrane. The elastomer composition of the matrix and membrane of the reservoir can be the same or different.

The invention is further illustrated by the following, non-limiting examples.

Experimental Part

The release rate of the therapeutically active substance from the device was measured in vitro as follows:

The devices (implant, intravaginal ring, intracervical or intrauterine system) were attached into a stainless steel holder in vertical position and the holders with the devices were placed into glass bottles containing 75 ml of a dissolution medium, a 1 wt-% hydroxypropyl cyclodextrin solution. The glass bottles were shaken in shaking waterbath 100 rpm at 37° C. The dissolution medium was withdrawn and replaced by a fresh dissolution medium at predetermined time intervals, and the amount of the released substance was analysed by using standard HPLC methods. The concentration of the dissolution medium and the moment of change (withdrawal and replacement) of medium were selected, so that sink-conditions were maintained during the test.

EXAMPLE 1

Danazol in Intravaginal Ring

The ability to control the initial burst effect was demonstrated with danazol, a synthetic androgen hormone (17alpha)-pregna-2,4-dien-20-yn[2,3-d]isoxazol-17-ol, by using an intravaginal ring (IVR) application in vitro for up to 32 days. Hydroxypropyl β-cyclodextrin (HPBCD) was used as the regulating agent. Three different implants with different hydroxypropyl β-cyclodextrin (HPBCD) contents in the membrane were made and the results were compared to corresponding implants without any added HPBCD. All the implants consisted of a core containing the therapeutically active agent and a release rate-controlling membrane encasing the core. The core and the membrane silicone elastomer rods were manufactured by extrusion and the implant compositions were made by swelling the membrane in propanol, as explained above. The content of the therapeutically active agent was 20 wt-% (weight percent) in the core and the micronized hormone was mixed into the elastomer with a mixer before extrusion. The diameters of the IVR rings were ca. 50-55 mm and the periphery of the cross section ca. 9-10 mm, the thicknesses of the membranes were 0.25, 0.35 and 0.7 mm and the HPBCD contents of the membrane were 0.17 wt-%, 1.7 wt-% and 7.7 wt-% respectively.

The results are shown in FIG. 1 for the daily in vitro release rate per core area ($\mu g/(d*mm^2)$, shown as the y axis and days shown in the x-axis), wherein the empty triangles represent the results for 0.17 wt-% HPBCD-content in the membrane with 0.7 mm wall thickness. The empty squares illustrate the results for 1.7 wt-% HPBCD-content in the membrane with 0.35 mm wall thickness and the stars show the results for 7.7 wt-% HPBCD-content in the membrane with 0.25 mm wall thickness. The full triangles represent the comparative results for a membrane with wall thickness of 0.3 mm and the full squares illustrate the comparative results for a membrane with wall thickness of 0.9 mm.

As seen in FIG. 1, HPBCD modification results in a significant improvement of reducing the initial burst of danazol from silicone based application. The initial burst effect found with all the HPBCD modified samples shows a negative initial burst effect. According to FIG. 1, the initial burst without the modification is five to ten times that found for modified samples and three to five times that found for the release rate in two weeks dissolution. The results show that without any regulating agent the magnitude of the initial burst is several times the release rate in the stable phase and the initial burst cannot be merely reduced by changing the formulation of the samples.

The release rate of the therapeutically active agent with HPBCD modified implants shows a slightly increasing trend for the first two weeks until it achieves a zenith point, where the release rate is at the maximum level. After that point the release rate of the therapeutically active agent presents a normal decreasing release profile as seen in the reference samples. For example the curve of empty triangles, with 0.17 w-% HPBCD content and 0.7 mm membrane wall, compared to an ordinary ring with 0.9 mm wall, shows that the release rate of the therapeutically active agent stays equal in two and half week release. However, according to the results the release rate seems to be higher, when HPBCD is added into the membrane.

EXAMPLE 2

Gestodene Implant

The present invention was also tested with an implant containing gestodene, a synthetic progestogene hormone. The implant core and membrane rods were made with extrusion and the implant composition was made by swelling the membrane in propanol. The outer diameter of the implant core was 2.5-3.0 mm and the length 40-48 mm. The content of the therapeutically active agent in the core was 65 wt-%. The membrane thickness was 0.25 mm, inner diameter 2.35-2.65 mm, outer diameter was 3.0-3.25 mm and length 10 mm longer than the elastomer core. The HPBCD content of the implant membrane was 4 wt-%. The membrane was made of PEO-b-PDMS (15 wt-%) and PDMS (85 wt-%).

Figure 2:
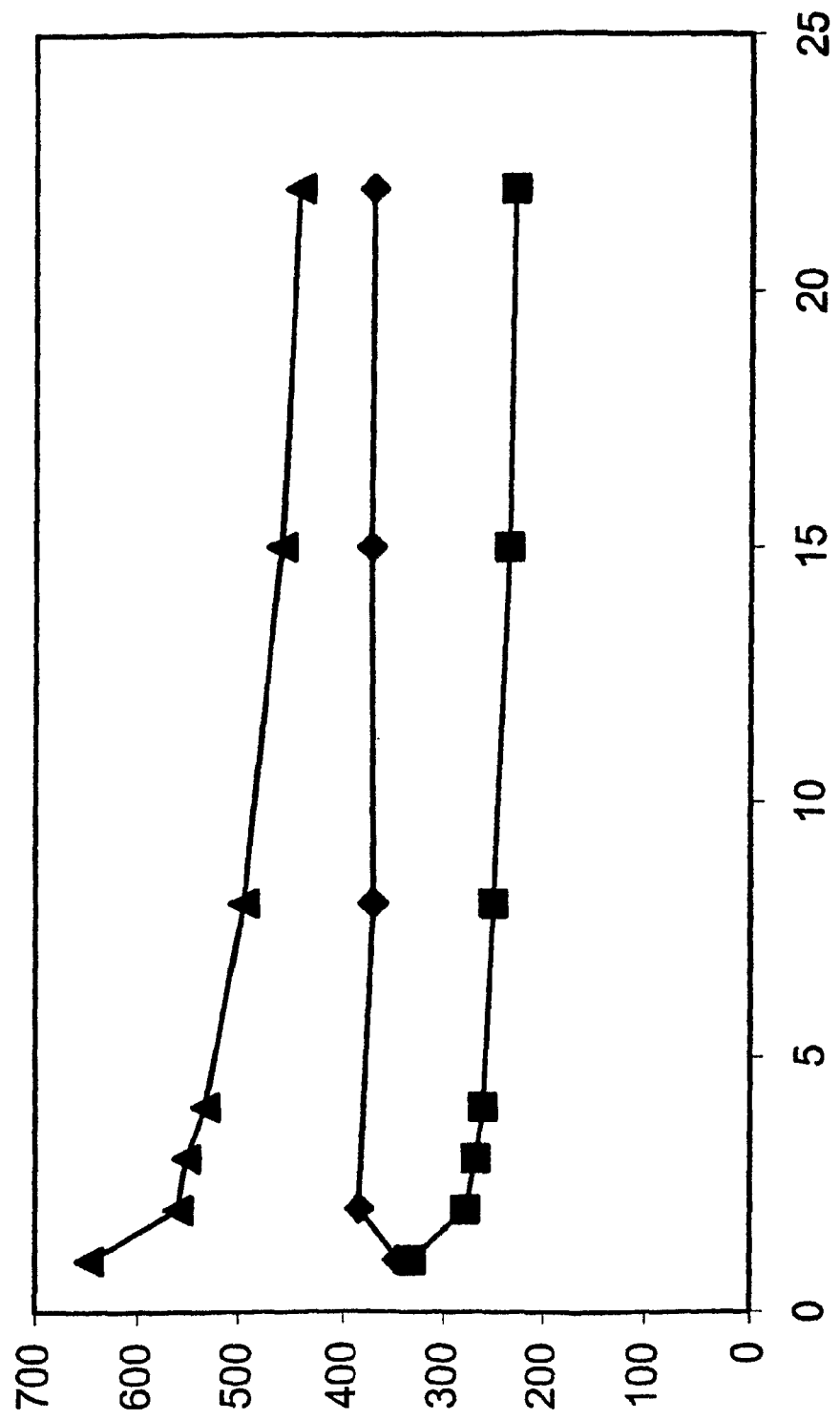
FIG. 2 illustrates the results of example 2.

The results are shown in FIG. 2 as the release rate of the therapeutically active agent ($\mu g/d$, shown in y-axis) versus time (days, shown in x-axis), wherein the squares represent the results for the Reference 1, the losanges represent the results for an implant having a HPBCD-containing membrane and the triangles illustrate the results for Reference 2. Reference 1 comprises a core having an outer diameter of 2.5 mm and a length of 40 mm, and a membrane, the thickness of which is 0.25 mm. The implant having a membrane containing 1 wt-% HPBCD has a core with an outer diameter of 3.03 mm and a length of 44 mm, and the membrane wall of 0.25 mm. Reference 2 comprises a core having an outer diameter of 2.8 mm, a length of 48 mm and the membrane with a wall of 0.25 mm.

Referring to FIG. 2, the release rate profiles of gestodene are smoother than previously presented for danazol in Example 1 as the total decrease of release was only 30% in 14 days with both reference samples. However, the cyclodextrin modification smoothed the release rates from the implants and the maximum decrease of release was only ca. 6% in two weeks. In addition to that, cyclodextrin modification seemed to stabilise the release rate of the therapeutically active agent after the initial burst, as the total decrease of the gestodene release was from the second to the third week only 0.5%, while for the reference samples the decrease was 8.4% and 11%.

EXAMPLE 3

Fluorinated Antiprogestin (FAP) in Intrauterine System (IUS)

HPBCD modification was tested with a fluorinated antiprogestin derivative (FAP, 11-(4-Acetylphenyl)-17-hydroxy-17-(1,1,2,2,2-pentafluoroethyl)estra-4,9-dien-3-one) in intrauterine (IUS) system. Two samples of 1 and 4 wt-% of HPBCD content in the membrane were prepared by combining with swelling separately extruded membrane and core elastomer rods over the IUS T-frame. The swelling agent was isopropanol.

Figure 3:
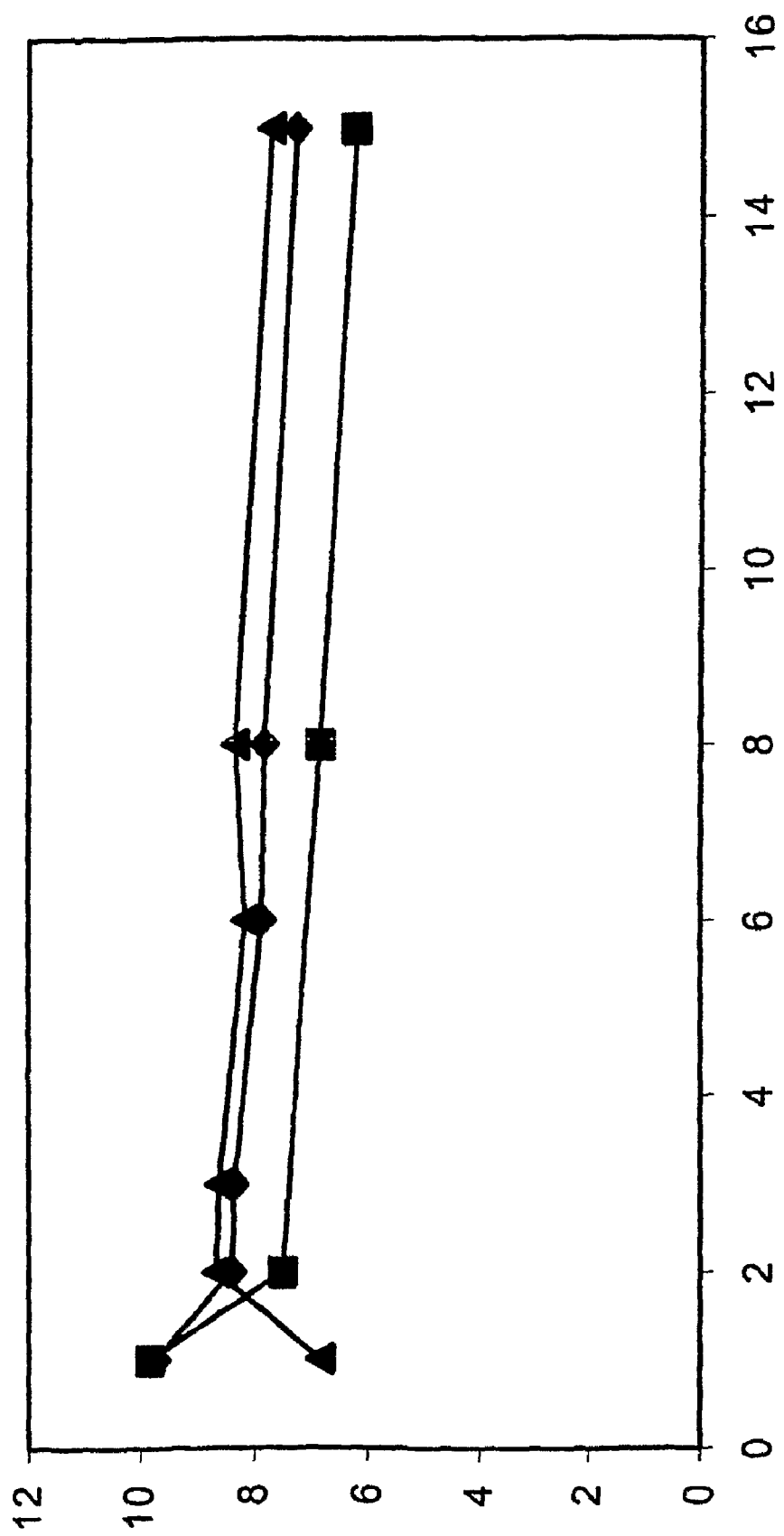
FIG. 3 illustrates the results of example 3.

The content of the therapeutically active agent in the core elastomer was 65 wt-% and the outer diameter of the core was 2.88-2.92 mm and length 21.0-21.1 mm. The membrane was 3 mm longer than the core and the thickness of the membrane was 0,25 mm. FIG. 3 presents the release rate of the therapeutically active agent ($\mu g/d$, shown in the y-axis) from two FAP containing intrauterine systems as a function of time (days, shown in the x-axis) compared to a reference sample. Indeed, the squares represent the results for the reference sample, the losanges illustrate the results for the cyclodextrin modified membrane, when the amount of cyclodextrin was 1 wt-% and the triangles represent the results for the cyclodextrin modified membrane, when the amount of cyclodextrin was 4 wt-%.

According to FIG. 3, the initial burst is decreased with both cyclodextrin-modified membranes. When the amount of cyclodextrin was 1 wt-%, there is still some burst effect remaining. In addition to that, the release rate profile of the therapeutically active agent is higher for both cyclodextrin modified samples than for the reference sample and the level of the release rate is higher, when the amount of cyclodextrin in the membrane was 4 wt-%. However, with FAP the profile, i.e. the shape of the curve, of the release rate after two days is similar for the reference and modified samples.

The invention claimed is:

1. A drug delivery system comprising a core and a membrane encasing said core, wherein said core and membrane consist essentially of an elastomer composition and said core comprises at least one therapeutically active agent, wherein the membrane comprises at least one regulating agent selected from the group consisting of cyclodextrins and modified cyclodextrins, and wherein said delivery system is selected from the group consisting of transdermal patches, implants for releasing a therapeutically active agent in the body tissues, intravaqinal rings, and intracervical and intrauterine devices.

2. The delivery system according to claim 1, wherein said regulating agent is selected from the group consisting of alpha cyclodextrins, beta cyclodextrins, gamma cylodextrins, hydroxypropyl cyclodextrins, maltosyl β-cyclodextrin and β-cyclodextrin sulfobutyl.

3. The delivery system according to claim 1, wherein the membrane comprises one regulating agent.

4. The delivery system according claim 1, wherein the membrane comprises two regulating agents.

5. The delivery system according to claim 4, wherein said regulating agents are present in separate parts of said membrane.

6. The delivery system according to claim 4, wherein said regulating agents are present in separate layers of said membrane.

7. A method for controlling the release of at least one therapeutically active agent from a drug delivery system comprising a core and a membrane encasing said core, wherein said core and membrane consist essentially of an elastomer composition and said core comprises said at least one therapeutically active agent, wherein said regulation is performed by at least one regulating agent comprised in the membrane of said delivery system, said regulating agent being selected from the group consisting of cyclodextrins and modified cyclodextrins, and wherein said delivery system is selected from the group consisting of transdermal patches, implants for releasing a therapeutically active agent in the body tissues, intravaqinal rings, and intracervical and intrauterine devices.

* * * * *